US006952604B2

(12) United States Patent
DeNuzzio et al.

(10) Patent No.: US 6,952,604 B2
(45) Date of Patent: Oct. 4, 2005

(54) MINIMALLY-INVASIVE SYSTEM AND METHOD FOR MONITORING ANALYTE LEVELS

(75) Inventors: John D. DeNuzzio, Chapel Hill, NC (US); William E. Strohben, Jr., Cary, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 22 days.

(21) Appl. No.: 10/024,506

(22) Filed: Dec. 21, 2001

(65) Prior Publication Data

US 2004/0015063 A1 Jan. 22, 2004

(51) Int. Cl.[7] .................................................. A61B 5/00
(52) U.S. Cl. ......................... 600/345; 600/347; 600/365
(58) Field of Search ................................. 600/345–350; 204/403

(56) References Cited

U.S. PATENT DOCUMENTS

| | | | |
|---|---|---|---|
| 2,154,003 A | 4/1939 | Lane | |
| 3,224,433 A | 12/1965 | Dalebor | |
| 3,436,329 A | 4/1969 | Kahn et al. | |
| 3,838,033 A | 9/1974 | Mindt et al. | |

(Continued)

FOREIGN PATENT DOCUMENTS

| | | |
|---|---|---|
| EP | 264210 | 10/1987 |
| EP | 320109 | 6/1989 |
| GB | 2154003 | 8/1985 |
| JP | 2120655 | 5/1990 |
| WO | 9846124 | 10/1998 |
| WO | WO9932174 | 1/1999 |
| WO | WO0010007 | 2/2000 |
| WO | WO01013102 | 2/2001 |

OTHER PUBLICATIONS

Buck, R. P.; Cosofret, V. V.; Lindner, E.; Ufer, S.; Madaras, M. B.; Johnson, T. A.; Ash, R. B., and Neuman, M. R. Microfabrication Technology of Flexible Membrane–Based Sensors for in–Vivo Applications. Electroanalysis. Sep. 1995; 7(9):846–851.

(Continued)

*Primary Examiner*—Robert L. Nasser
(74) *Attorney, Agent, or Firm*—Roylance, Abrams, Berdo & Goodman, L.L.P.

(57) ABSTRACT

A minimally-invasive analyte detecting device and method for using the same. The system and method employ a device having an active electrode optionally coated with a substance, and a counter-electrode that is configured at least partially surround the active electrode. The configuration of the auxiliary electrode and active electrode improves the current flow through the device and increases the sensitivity of the device. When the device is placed against the patient's skin, the active electrode is adapted to enter through the stratum corneum of a patient to a depth less than a depth in the dermis at which nerve endings reside. An electric potential is applied to the active electrode and the analyte level is determined based on the amount of current or charge flowing through the device.

23 Claims, 6 Drawing Sheets

U.S. PATENT DOCUMENTS

| | | | |
|---|---|---|---|
| 3,857,771 A | 12/1974 | Sternberg | |
| 3,912,614 A | 10/1975 | Spracklen et al. | |
| 3,923,627 A | * 12/1975 | Niedrach et al. | 204/414 |
| 3,948,745 A | 4/1976 | Guilbault et al. | |
| 4,071,020 A | 1/1978 | Pugliese | |
| 4,198,280 A | 4/1980 | Swartz | |
| 4,425,918 A | 1/1984 | Moll et al. | |
| 4,431,004 A | 2/1984 | Bessman et al. | |
| 4,436,094 A | 3/1984 | Cerami | |
| 4,440,175 A | 4/1984 | Wilkins | |
| 4,452,249 A | 6/1984 | Sachs et al. | |
| 4,458,685 A | 7/1984 | Hiramoto et al. | |
| 4,458,686 A | 7/1984 | Clark, Jr. et al. | |
| 4,494,950 A | 1/1985 | Fischell | |
| 4,539,994 A | 9/1985 | Baumbach et al. | |
| 4,545,382 A | 10/1985 | Higgins et al. | |
| 4,622,974 A | 11/1986 | Coleman et al. | |
| 4,627,445 A | 12/1986 | Garcia et al. | |
| 4,637,403 A | 1/1987 | Garcia et al. | |
| 4,643,193 A | 2/1987 | DeMarzo | |
| 4,650,547 A | 3/1987 | Gough | |
| 4,671,288 A | 6/1987 | Gough | |
| 4,674,499 A | * 6/1987 | Pao | 606/50 |
| 4,679,562 A | 7/1987 | Luksha | |
| 4,685,465 A | 8/1987 | Klitgaard et al. | |
| 4,685,466 A | 8/1987 | Rau | |
| 4,703,756 A | 11/1987 | Gough et al. | |
| 4,711,245 A | 12/1987 | Higgins et al. | |
| 4,784,145 A | 11/1988 | Ahsbahs et al. | |
| 4,805,624 A | 2/1989 | Yao et al. | |
| 4,820,399 A | 4/1989 | Senda et al. | |
| 4,821,733 A | 4/1989 | Peck | |
| 4,890,620 A | 1/1990 | Gough | |
| 4,909,908 A | 3/1990 | Ross et al. | |
| 4,919,141 A | 4/1990 | Zier et al. | |
| 4,932,410 A | 6/1990 | Lacourciere et al. | |
| 4,935,346 A | 6/1990 | Phillips et al. | |
| 4,953,552 A | * 9/1990 | DeMarzo | 600/347 |
| 4,960,467 A | 10/1990 | Peck | |
| 4,970,145 A | 11/1990 | Bennetto et al. | |
| 4,986,271 A | 1/1991 | Wilkins | |
| 4,994,167 A | 2/1991 | Shults et al. | |
| 4,995,391 A | 2/1991 | Jensen et al. | |
| 5,000,180 A | 3/1991 | Kuypers et al. | |
| 5,002,054 A | 3/1991 | Ash et al. | |
| 5,007,424 A | 4/1991 | Ahsbahs et al. | |
| 5,014,718 A | 5/1991 | Mitchen | |
| 5,036,861 A | 8/1991 | Sembrowich et al. | |
| 5,054,499 A | 10/1991 | Swierczek | |
| 5,076,273 A | 12/1991 | Schoendorfer et al. | |
| 5,089,112 A | 2/1992 | Skotheim et al. | |
| 5,139,023 A | 8/1992 | Stanley et al. | |
| 5,140,985 A | 8/1992 | Schroeder et al. | |
| 5,161,532 A | 11/1992 | Joseph | |
| 5,165,406 A | 11/1992 | Wong | |
| 5,165,407 A | 11/1992 | Wilson et al. | |
| 5,171,689 A | 12/1992 | Kawaguri et al. | |
| 5,201,324 A | 4/1993 | Swierczek | |
| 5,203,327 A | 4/1993 | Schoendorfer et al. | |
| 5,262,035 A | 11/1993 | Gregg et al. | |
| 5,269,891 A | * 12/1993 | Colin | 205/777.5 |
| 5,279,543 A | 1/1994 | Glikfeld et al. | |
| 5,298,022 A | 3/1994 | Bernardi | |
| 5,299,571 A | 4/1994 | Mastrototaro | |
| 5,306,294 A | 4/1994 | Winston et al. | |
| 5,320,607 A | 6/1994 | Ishibashi | |
| 5,322,063 A | 6/1994 | Allen et al. | |
| 5,356,786 A | 10/1994 | Heller et al. | |
| 5,362,307 A | 11/1994 | Guy et al. | |
| 5,390,671 A | 2/1995 | Lord et al. | |
| 5,411,551 A | 5/1995 | Winston et al. | |
| 5,431,160 A | 7/1995 | Wilkins | |
| 5,445,920 A | 8/1995 | Saito | |
| 5,458,140 A | 10/1995 | Eppstein et al. | |
| 5,497,772 A | 3/1996 | Schulman et al. | |
| 5,509,410 A | 4/1996 | Hill et al. | |
| 5,510,266 A | 4/1996 | Bonner et al. | |
| 5,527,334 A | * 6/1996 | Kanner et al. | 606/182 |
| 5,568,806 A | 10/1996 | Cheney, II et al. | |
| 5,580,431 A | 12/1996 | Isaacs et al. | |
| 5,582,184 A | 12/1996 | Erickson et al. | |
| 5,593,852 A | 1/1997 | Heller et al. | |
| 5,611,900 A | 3/1997 | Worden et al. | |
| 5,617,851 A | 4/1997 | Lipkovker | |
| 5,628,890 A | 5/1997 | Carter et al. | |
| 5,660,163 A | 8/1997 | Schulman et al. | |
| 5,672,256 A | 9/1997 | Yee | |
| 5,680,858 A | 10/1997 | Hansen et al. | |
| 5,682,233 A | 10/1997 | Brinda | |
| 5,682,884 A | 11/1997 | Hill et al. | |
| 5,694,932 A | 12/1997 | Michel | |
| 5,695,623 A | 12/1997 | Michel et al. | |
| 5,704,354 A | 1/1998 | Preidel et al. | |
| 5,708,247 A | 1/1998 | McAleer et al. | |
| 5,722,397 A | 3/1998 | Eppstein | |
| 5,727,548 A | 3/1998 | Hill et al. | |
| 5,728,074 A | 3/1998 | Castellano et al. | |
| 5,730,714 A | 3/1998 | Guy et al. | |
| 5,735,273 A | 4/1998 | Kurnik et al. | |
| 5,746,217 A | 5/1998 | Erickson et al. | |
| 5,749,832 A | 5/1998 | Vadgama et al. | |
| 5,762,770 A | 6/1998 | Pritchard et al. | |
| 5,770,028 A | 6/1998 | Maley et al. | |
| 5,771,890 A | 6/1998 | Tamada | |
| 5,773,270 A | 6/1998 | D'Orazio et al. | |
| 5,779,867 A | 7/1998 | Shieh | |
| 5,791,344 A | 8/1998 | Schulman et al. | |
| 5,798,031 A | 8/1998 | Charlton et al. | |
| 5,800,420 A | 9/1998 | Gross et al. | |
| 5,804,048 A | 9/1998 | Wong et al. | |
| 5,806,517 A | 9/1998 | Gerhardt et al. | |
| 5,807,375 A | 9/1998 | Gross et al. | |
| 5,820,551 A | 10/1998 | Hill et al. | |
| 5,820,570 A | 10/1998 | Erickson et al. | |
| 5,820,622 A | 10/1998 | Gross et al. | |
| 5,827,183 A | 10/1998 | Kurnik et al. | |
| 5,842,713 A | 12/1998 | Barnes et al. | |
| 5,842,983 A | 12/1998 | Abel et al. | |
| 5,876,577 A | 3/1999 | McAleer et al. | |
| 5,879,310 A | 3/1999 | Sopp et al. | |
| 5,879,311 A | 3/1999 | Duchon et al. | |
| 5,879,367 A | 3/1999 | Latterell et al. | |
| 5,913,833 A | 6/1999 | Elstrom et al. | |
| 5,914,026 A | * 6/1999 | Blubaugh et al. | 600/347 |
| 5,916,156 A | 6/1999 | Hildenbrand et al. | |
| 5,925,021 A | 7/1999 | Castellano et al. | |
| 5,930,671 A | 7/1999 | Ku | |
| 5,944,661 A | 8/1999 | Swette et al. | |
| 5,951,492 A | 9/1999 | Douglas et al. | |
| 5,951,836 A | 9/1999 | McAleer et al. | |
| 5,954,643 A | 9/1999 | Van Antwerp et al. | |
| 5,954,685 A | 9/1999 | Tierney | |
| 5,964,718 A | 10/1999 | Duchon et al. | |
| 5,965,380 A | 10/1999 | Heller et al. | |
| 5,985,116 A | 11/1999 | Ikeda et al. | |
| 5,989,409 A | 11/1999 | Kurnik et al. | |
| 5,993,411 A | 11/1999 | Choi | |
| 6,001,239 A | 12/1999 | Douglas et al. | |
| 6,014,577 A | 1/2000 | Henning et al. | |
| 6,015,392 A | 1/2000 | Douglas et al. | |
| 6,022,316 A | 2/2000 | Eppstein et al. | |

| | | |
|---|---|---|
| 6,023,629 A | 2/2000 | Tamada |
| 6,023,630 A | 2/2000 | Bacchi et al. |
| 6,023,639 A | 2/2000 | Hakky et al. |
| 6,030,827 A | 2/2000 | Davis et al. |
| 6,033,866 A | 3/2000 | Guo et al. |
| 6,036,924 A | 3/2000 | Simons et al. |
| 6,048,232 A | 4/2000 | Chen |
| 6,048,352 A | 4/2000 | Douglas et al. |
| 6,056,701 A | 5/2000 | Duchon et al. |
| 6,063,039 A | 5/2000 | Cunningham et al. |
| 6,064,900 A | 5/2000 | Vadgama et al. |
| 6,066,103 A | 5/2000 | Duchon et al. |
| 6,071,249 A | 6/2000 | Cunningham et al. |
| 6,071,294 A | 6/2000 | Simons et al. |
| 6,071,391 A | 6/2000 | Gotoh et al. |
| 6,077,660 A | 6/2000 | Wong et al. |
| 6,080,116 A | 6/2000 | Erickson et al. |
| 6,083,710 A | 7/2000 | Heller et al. |
| 6,091,975 A | 7/2000 | Daddona et al. |
| 6,093,156 A | 7/2000 | Cunningham et al. |
| 6,096,497 A | 8/2000 | Bauer |
| 6,099,484 A | 8/2000 | Douglas et al. |
| 6,104,940 A * | 8/2000 | Watanabe et al. ............ 600/345 |
| 6,106,780 A | 8/2000 | Douglas et al. |
| 6,108,570 A | 8/2000 | Kohen et al. |
| 6,120,464 A | 9/2000 | Racchini et al. |
| 6,120,676 A | 9/2000 | Heller et al. |
| 6,121,009 A | 9/2000 | Heller et al. |
| 6,123,819 A | 9/2000 | Peeters |
| 6,134,461 A | 10/2000 | Say et al. |
| 6,136,008 A * | 10/2000 | Becker et al. ............... 606/131 |
| 6,139,718 A | 10/2000 | Kurnik et al. |
| 6,141,573 A | 10/2000 | Kurnik et al. |
| 6,143,164 A | 11/2000 | Heller et al. |
| 6,144,869 A | 11/2000 | Berner et al. |
| 6,148,232 A | 11/2000 | Avrahami |
| 6,152,889 A | 11/2000 | Sopp et al. |
| 6,153,069 A | 11/2000 | Pottgen et al. |
| 6,155,992 A | 12/2000 | Henning et al. |
| 6,156,173 A | 12/2000 | Gotoh et al. |
| 6,162,611 A | 12/2000 | Heller et al. |
| 6,168,699 B1 | 1/2001 | Frenkel et al. |
| 6,175,752 B1 | 1/2001 | Say et al. |
| 6,176,988 B1 | 1/2001 | Kessler |
| 6,180,416 B1 | 1/2001 | Kurnik et al. |
| 6,201,979 B1 | 3/2001 | Kurnik et al. |
| 6,233,471 B1 | 5/2001 | Berner et al. |
| 6,272,364 B1 | 8/2001 | Kurnik |
| 6,275,717 B1 | 8/2001 | Gross et al. |
| 6,284,126 B1 | 9/2001 | Kurnik et al. |
| 6,298,254 B2 | 10/2001 | Tamada |
| 6,299,578 B1 | 10/2001 | Kurnik et al. |
| 6,309,351 B1 | 10/2001 | Kurnik et al. |
| 6,326,160 B1 | 12/2001 | Dunn et al. |
| 6,332,871 B1 | 12/2001 | Douglas et al. |
| 6,341,232 B1 | 1/2002 | Conn et al. |
| 6,356,776 B1 | 3/2002 | Berner et al. |
| 6,370,410 B2 | 4/2002 | Kurnik et al. |
| 6,391,643 B1 | 5/2002 | Chen et al. |
| 6,393,318 B1 | 5/2002 | Conn et al. |
| 6,501,976 B1 * | 12/2002 | Sohrab ...................... 600/347 |
| 6,558,320 B1 * | 5/2003 | Causey et al. .............. 600/300 |
| 2001/0003045 A1 | 6/2001 | Davis et al. |

OTHER PUBLICATIONS

Jung, S. K.; Gorski, W.; Aspinwall, C. A.; Kauri, L. M., and Kennedy, R. T. Oxygen Microsensor and Its Application to Single Cells and Mouse Pancreatic Islets. Analytical Chemistry. Sep. 1, 1999; 71(17):3642–3649.

Chen, C Y; Tamiya, E; Ishihara, K; Kosugi, Y; Su, Y C; Nakabayashi, N, and Karube, I. A Biocompatible Needle–Type Glucose Sensor Based On Platinum–Electroplated Carbon Electrode. Applied Biochemistry and Biotechnology. Sep. 1992: 36(3):211–226.

Chen, Chien–Yuan; Gotoh, Masao; Makino, Hideichi; Su, Yuan–Chi; Tamiya, Eiichi, and Karube, Isao. Amperometric Needle–Type Glucose Sensor Based On A Modified Platinum Electrode With Diminished Response To Interfering Materials. Analytica Chimica Acta Aug. 1, 1992: 265(1):5–14.

Ishikawa, Masahiko; Schmidtke, David W.; Raskin, Philip, and Quinn, Christopher A. P. Initial Evaluation of a 290–[mu]m Diameter Subcutaneous Glucose Sensor, ; Glucose Monitoring with a Biocompatible, Flexible–Wire. Enzyme–Based Amperometric Microsensor in Diabetic and Nondiabetic.

Shichiri, M; Asakawa, N; Yamasaki, Y; Kawamori, R, and Abe, H. Telemetry Glucose Monitoring Device With Needle–Type Glucose Sensor: A Useful Tool For Blood Glucose Monitoring In Diabetic Individuals. Diabetes Care. 9(3):298–301.

Yang, Qingling; Atanasov, Plamen, and Wilkins, Ebtisam. Development Of Needle–Type Glucose Sensor With High Selectivity. Sensors and Actuators B: Chemical. May 15, 1998; 46(3):249–256.

Zen, J. M.; Kumar, A. S., and Wang, H. F. A Dual Electrochemical Sensor for Nitrite and Nitric Oxide. Analyst. 2000; 125(12):2169–2172.

Gorski et al., J.Electroanalytical Chem., "Ruthenium Catalyst for Amperometric Determination of Insulin at Physiological pH," 425 (1–2) :191–199 (1997).

* cited by examiner

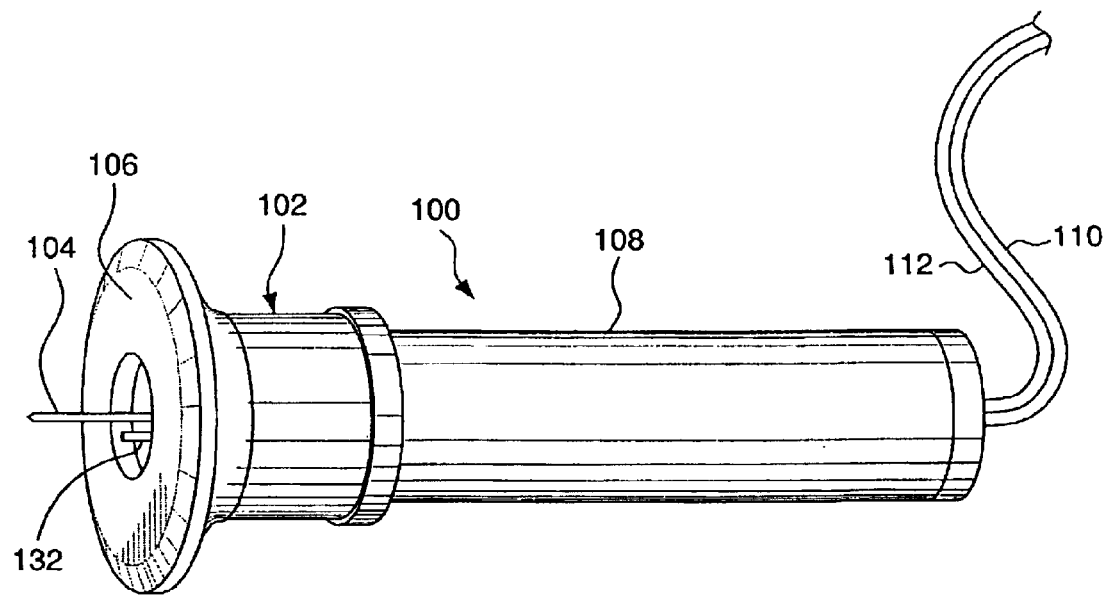
FIG. 9
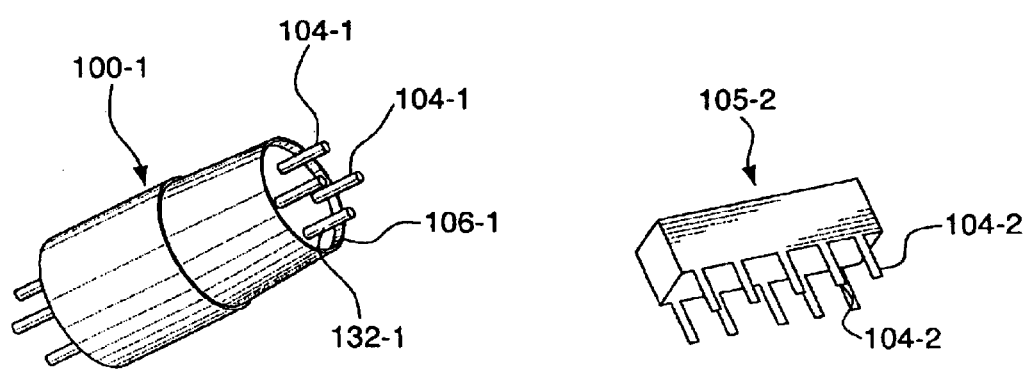
FIG. 10
FIG. 11

MINIMALLY-INVASIVE SYSTEM AND METHOD FOR MONITORING ANALYTE LEVELS

BACKGROUND THE INVENTION

1. Field of the Invention

The present invention relates to a minimally-invasive system and method for monitoring analyte levels in a patient. More particularly, the present invention relates to a system and method employing a device which includes a micro probe functioning as an active electrode and a auxiliary electrode surrounding at least a portion of the active electrode, arranged to be placed against the skin of a patient to detect analyte levels in the patient with minimal pain and damage to the patient's skin.

2. Description of the Related Art

People having diabetes must monitor their blood glucose level on a regular basis to assure that their blood glucose level remains within normal limits necessary to maintain a healthy living condition. Low glucose levels, known as hypoglycemia, can cause mental confusion and, in more extreme instances, coma and ultimately death. On the other hand, high blood glucose levels, known as hypoglycemia, can cause chronic symptoms such frequent urination and thirst, and if sustained over long periods of time, can result in damage to blood vessels, eyes, kidneys and other organs of the body.

Some people having mild diabetes can regulate their blood glucose levels through diet. However, people having moderate or severe forms of diabetes must take insulin to sustain acceptable blood glucose levels.

Conventional methods of monitoring blood glucose levels directly monitor the concentration of glucose in a small sample of blood taken from the person. Accordingly, if the person wishes to test his or her blood glucose level, the person can use a small needle or lance to puncture, for example his or her fingertip and drain a droplet of blood into the sampling device. However, this invasive method is painful to the person. Moreover, precautions must be taken sterilize the area in which the puncture is made, as well as the puncturing instrument, so that a pathogen is not introduced into the person's bloodstream. These methods can also be somewhat messy and unsanitary, and somewhat time consuming.

As an alternative to the conventional invasive techniques, miniaturized glucose sensing needles have been developed over the past several years. These types of devices typically include a metal substrate with an enzyme as an active electrode and an adjacent metal substrate that serve as the return and reference electrodes. The enzyme, typically glucose oxidase, catalyzes the oxidation of glucose, and the byproducts of the reaction are measured electrochemically at the active electrode. The electrochemical measurement is affected by imposing an electrical potential between the active and the counter/reference (auxiliary) electrodes. At a particular potential, electric current begins to flow as a consequence of the chemical reaction at the electrodes. The current is related to the concentration of the electro-active species, which is in turn governed by the amount of glucose in the test medium. In the case of conventional glucose strips, the test medium is capillary blood; in the case of implantable electrodes, the medium is tissue.

These devices are typically macroscopic or, in other words, more than 200 microns in diameter and often a centimeter or more in length. Accordingly, these devices are invasive, because they can penetrate the skin up to one centimeter deep. Additionally, these devices typically employ conventional needles, wires and multi-layer plastic substrates which require complicated multi-step manufacturing processes that are both time consuming and expensive. Examples of known glucose sensing devices are described in U.S. Pat. Nos. 4,953,552, 5,680,858 and 5,820,570, and in PCT publication WO 98/46124.

Maximizing the active electrode area increases the current response of the system. Especially in the case of the implantable system, the active electrode area is small—often tenfold smaller than strip-based electrodes. Furthermore, the active and return/reference electrodes often share the same substrate—further limiting the available active area. One advantage of the invention described herein is that the return electrode is separated from the active electrode substrate and can be positioned on the surface of the skin, at least partially surrounding the minimally-invasive working electrode. This configuration allows maximum usage of the active electrode, and it permits the use of a large external return electrode. Both aspects improve the signal and performance of the system, while maintaining the small minimally invasive, pain-free format of the design.

Accordingly, a need exists for an improved minimally invasive system for monitoring analyte levels in patients.

SUMMARY OF THE INVENTION

The present invention relates to a system and method for detecting an analyte component, such as glucose, in a patient. The system and method employ a device comprising an active electrode optionally coated with a substance, such as glucose oxidase, and a counter-electrode that is configured to surround at least a portion of the active electrode. The configuration of the counter and active electrode improves the current flow through the device and increases the sensitivity of the device. When the device and method are used to detect the analyte of a patient, the active electrode may have a portion thereof adjacent to a substance, for example, glucose oxidase, and a length such that when the device is placed against the patient's skin, the active electrode is adapted to pass through the stratum corneum of the patient, preferably to a depth at which few nerve endings reside, to enable the analyte in the patient to be electrochemically detected, either directly or, for example, by reaction with a substance on the portion of the active electrode to produce an electrochemically detectable species. As stated above, the auxiliary electrode is configured to surround at least a portion of the active electrode, and is adapted to contact the patient's skin when the device is placed against the patient's skin. The active electrode extends beyond a base portion of the device to a length suitable to access the analyte, and the auxiliary electrode is coupled to a surface of the base portion proximate to that from which the active electrode extends. The active electrode is further adapted to have applied to its electric potential to measure a reaction between the analyte in the patient and the substance adjacent to the active electrode. The device can further include a reference electrode, disposed at a distance from the active electrode less than or equal to a distance between the active electrode and any portion of the auxiliary electrode, or adjacent to the active electrode, or integral with the auxiliary electrode, so that the reference electrode acts as a reference potential for the electrical potential applied to the active electrode. The reference electrode can thus be used to compensate for changes in resistivity of the skin which can effect the accuracy of the device.

BRIEF DESCRIPTION OF THE DRAWINGS

These and other features and advantages of the present invention will be more readily appreciated from the following detailed description when read in conjunction with the appended drawings, in which:

FIG. 9 illustrates an example of an analyte detecting device, as shown in FIG. 1, having a reference electrode;

FIG. 10 is an example of an analyte detecting device according to another embodiment of the present invention;

FIG. 11 is an example of a strip of active electrodes for the analyte detecting device according to a further embodiment of the present invention.

DETAILED DESCRIPTION OF THE PREFERRED EMBODIMENTS

Figure 1:
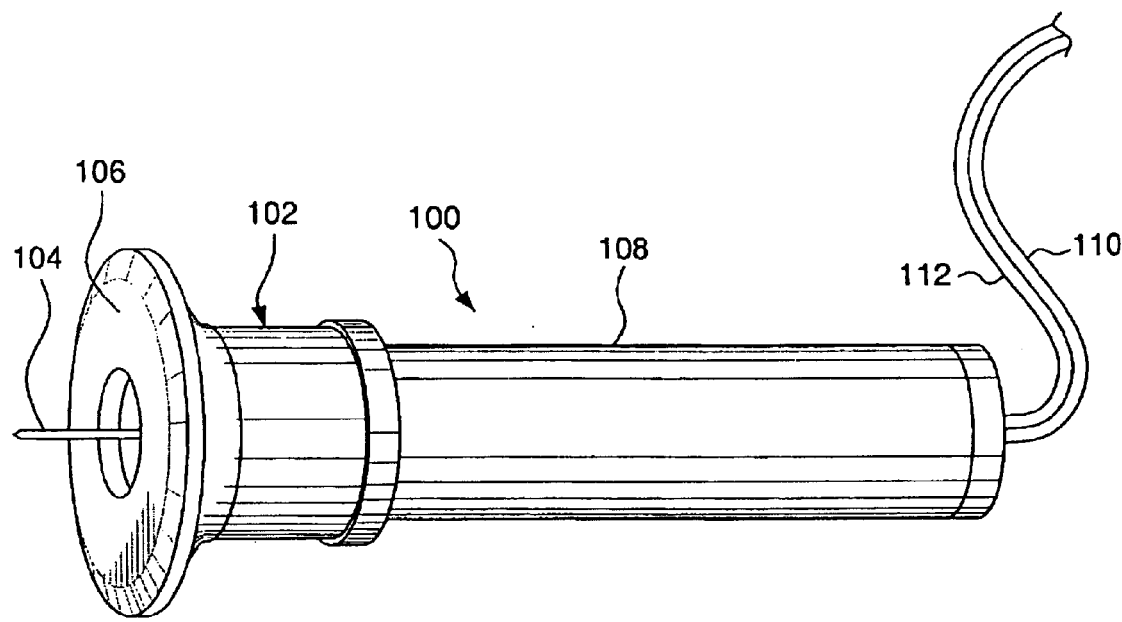
FIG. 1 illustrates an example of a analyte detecting device according to an embodiment of the present invention.

FIGS. 1–6 illustrate an analyte detecting device 100 according to an embodiment of the present invention. As shown in FIG. 1, the device 100 includes a base portion 102 which employs an active electrode 104 and an auxiliary electrode and or in combination therewith, a reference electrode 106 which are described in more detail below. As used herein, the terms counter or reference electrode include combinations thereof as is known in the art. The base portion 102 is connected to a housing 108 that extends along the lengthwise direction of the device 100. The base portion 102 and housing 108 can therefore act as the base of the device 100 that can be held during operation as described in more detail below. The base portion 102 can be fixed or pivotable with respect to the axis of active electrode 104 to any angle, by various means, for example, by constructing base portion 102 from an elastic material or providing a joint such that the active electrode can be inserted at a angle less than or about 90 degrees when the auxiliary electrode 106 is positioned substantially parallel and adjacent to the skin of a patient.

Figure 2:
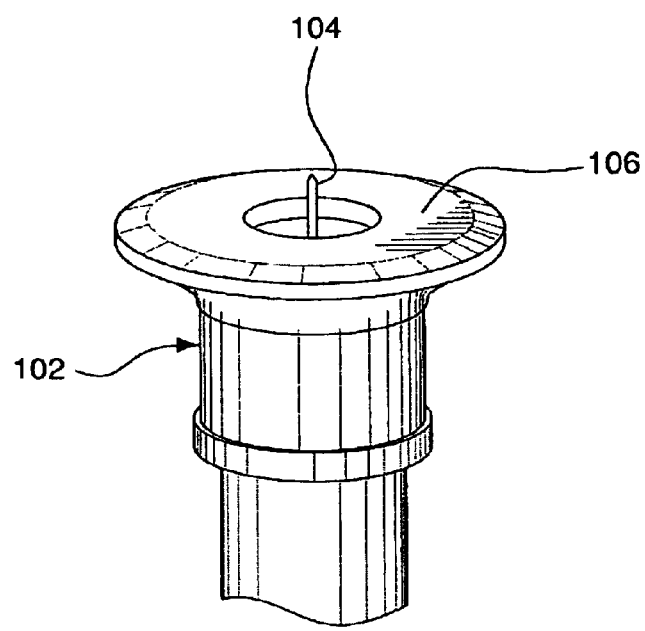
FIG. 2 is a detailed view of the distal end of the analyte detecting device shown in FIG. 1.
Figure 3:
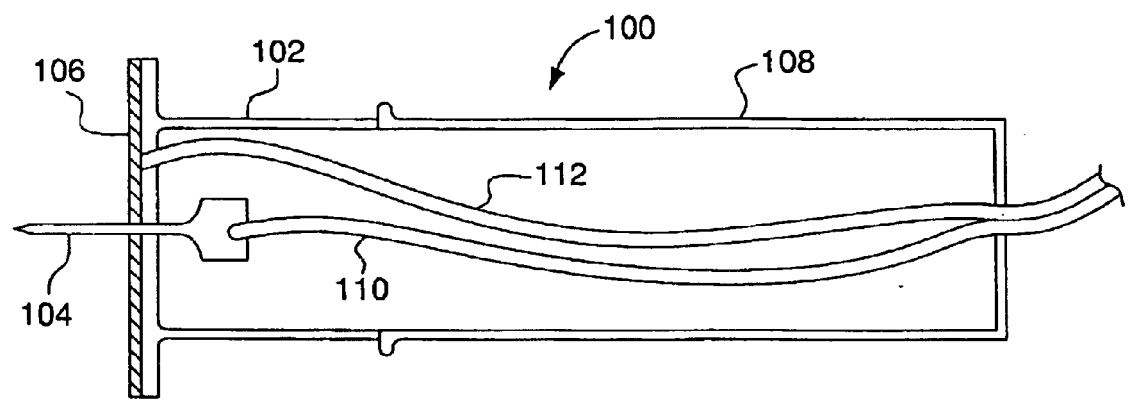
FIG. 3 is a cross-sectional view of the analyte detecting device shown in FIG. 1.
Figure 4:
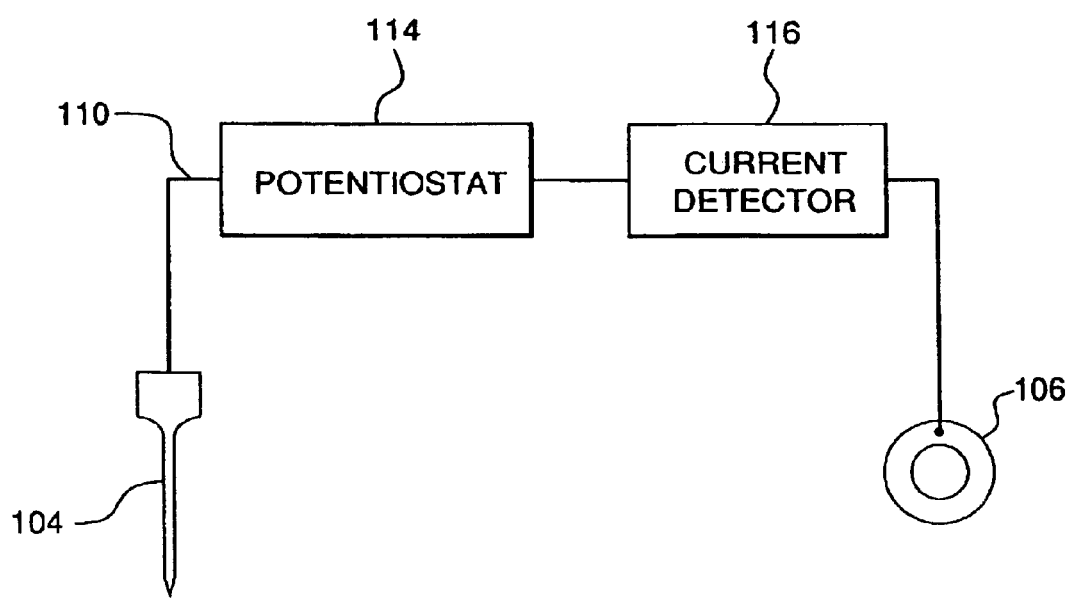
FIG. 4 is an exemplary electrical schematic of the components employed in or used in conjunction with the analyte detecting device shown in FIG. 1.

As shown in exemplary FIGS. 1–3 the active electrode 104 may be located along the axial center or substantially along the axial center of the device 100. Also, an auxiliary electrode 106, which may be circular or substantially circular, extends entirely around the active electrode 104. Active electrode may alternatively be automatically or manually extendable from the base portion 102 either manually or by mechanical means to insert at least a portion of active electrode 104 through the stratum corneum at any angle greater than zero up to about 90 degrees relative to the surface of the skin to which it is applied. The auxiliary electrode 106 can be made entirely of, or be combinations thereof, of any suitable base material, either conductive or non-conductive, such a silicon, plastic, or a metal, or optionally a non-conductive material coated with a conductive material, such as gold, platinum, graphite, palladium, or the like, including thin metal foils or films or metal foils or films supported on plastic, paper, or other flexible material. The auxiliary electrode 106 can extend around the entire circumference of the base portion 102 of the device 100 as shown in FIGS. 1 and 2, or can extend along any suitable portion of the circumference of the base portion 102 so as to encircle the active electrode 104 either entirely or partially. The auxiliary electrode 106 can also be divided into several semi-circular or arcuate shapes. Alternatively, the auxiliary electrode 106 need not be circular, but can be any suitable shape such as square, rectangular, oval, or can be any suitable pattern of electrodes. Furthermore, the auxiliary electrode 106 can be configured as to contain adjacent to at least a portion of the surface, a conductive gel material or any other suitable conductive material or device. Auxiliary electrode 106 can be of suitable construction to provide for conforming closely and or securely to the skin, including the use of adhesive means generally know in the art. Auxiliary electrode 106 can also include an abrasive surface which can slightly abrade the surface of the patient's skin, as well as the stratum corneum, to thus establish better electrical contact with the patient. Furthermore, the auxiliary electrode 106 can be configured to be minimally invasive to the patient's skin as is the active electrode 104.

An exemplary device is shown in FIG. 3, whereby the active electrode 104 may be coupled to a conductor 110 that extends along the hollow interiors of the base portion 102 and housing 108 of the device 100, while auxiliary electrode 106 is coupled to a conductor 112 that also extends along the hollow interiors of the base portion 102 and housing 108 of the device 100. Alternatively, the base portion 102 and housing 108 of the device 100 may be flat or of open-structure to lie substantially flat. Conductors 110 or 112 are electrically insulated from each other. An exemplary device, as illustrated schematically in FIG. 4, has the active electrode 104 and the counter-electrode 106 coupled to a voltage generating device, such as a potentiostat 114, and a current detector 116, the purposes of which are described in more detail below.

Figure 5:
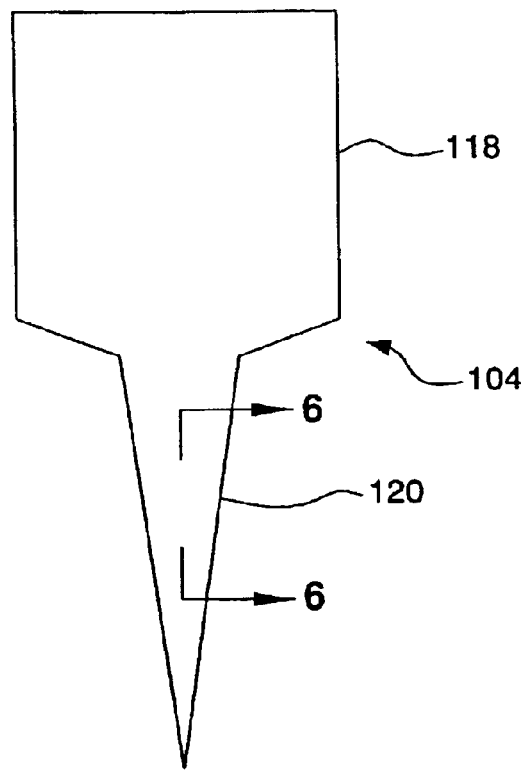
FIG. 5 is detailed view of an example of an active electrode employed in the analyte detecting device shown in FIG. 1.

As shown in FIG. 5, the active electrode 104 can have a tab portion 118 and a probe portion 120. In this example, the tab portion 118 can be square-shaped or substantially square-shaped having a width of 1 mm or about 1 mm and a length of 1 mm or about 1 mm. The probe portion 120 can have a length ranging from at or about 20 $\mu$m to at or about 5000 $\mu$m. However, the length of the probe portion 120 is preferably small, for example, at or about 100–2000 $\mu$m, so as to be minimally invasive when inserted in the patient's skin as described in more detail below. In addition, the diameter of the tip of probe 120 is substantially small, for example 100–250 $\mu$m or less. Also, the active electrode 104 need not have the configuration shown in FIG. 5, but rather, can be shaped as a needle, microlance, microneedle, or have any other suitable shape to provide access through the stratum corneum.

Furthermore, the active electrode 104 can be disposable, that is, used once and replaced with another fresh active electrode 104. In other words, the active electrode 104 can be removably coupled to the conductor via, for example, a socket arrangement (not shown) so that after use, the active electrode 104 can be removed from the device 100 by hand or through the use of an instrument, and discarded. Alternatively, the device 100 can be configured with an ejection tool (not shown) which ejects the active electrode 104. Once the used active electrode 104 has been removed or ejected, another active electrode 104 can be inserted into the device 100.

Also, as discussed in more detail below with regard to FIGS. 11 and 12, the device 100 can be configured with a supply of active electrodes 104, which can be selectably fed to an active location such as that shown in FIG. 1, and then discarded after use. Likewise, the auxiliary electrode 106 can be reusable or disposable. In addition, the device 100 can be configured with a retractable mechanism (not shown) that can be controlled to extend the active electrode 104 from the distal end of the device 100 so that the active electrode 104 can enter the patient's stratum corneum when the distal end of the device is placed against the patient's skin as can be appreciated by one skilled in the art. The retractable mechanism can further be controlled to retract the active electrode 104 back into an opening in the distal end of the device 100 after use. Alternatively, the retractable mechanism can be configured as an ejection mechanism to eject the active electrode 104 after use so that a fresh active electrode 104 can be installed.

Figure 6:
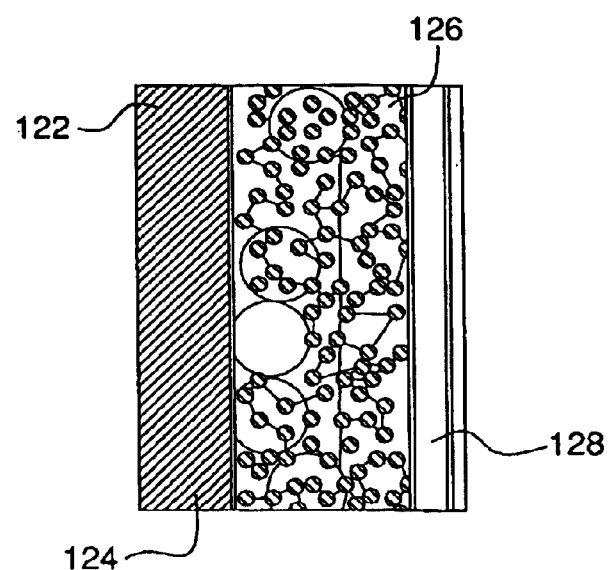
FIG. 6 is a detailed cross-sectional view of a portion of the active electrode shown in FIG. 5.

FIG. 6 is a cross-sectional view of a portion of an exemplary probe portion 120 of the active electrode 104 as shown in FIG. 5. As illustrated, the probe portion 120 is made of a base material 122, such a silicon substrate, stainless steel, plastic, or any other suitable material. The base material 122 is coated with a conductor, such as platinum, gold, graphite, palladium, or any other suitable material 124. For example, the base material 122 can be sputter-coated with platinum to form the conductive layer 124. A substance 126 adjacent to at least a portion of 124, for example, glucose oxidase containing layer 126, is applied to the conductive layer 124 in an immobilization matrix as illustrated. For example, the glucose oxidase can be dissolved in aqueous media and dispensed onto conductive layer 124 followed by exposure to glutaraldehyde solution, and allow to dry. Upon drying, the glucose oxidase enzyme becomes cross-linked on the surface of the base material 122. Or the enzyme can be immobilized by spin coating an aqueous solution of enzyme and a UV crosslinkable polyvinyl alcohol modified polymer. An interference film 128 can then be applied over the glucose oxidase layer 126 as shown. Glucose oxidase enzyme immobilization methods and interference films for reducing extraneous signal from electro-active species found in biological fluids are well known in the art. Additionally, mediators can be included in the layer 126 as is known in the art.

It is also noted that the active electrode 104 can be coated with differed types or combinations of enzymes, such as glucose oxidase, dehydrogenase, lactate dehydrogenase, and so on, and can use non-enzymatic molecular recognition chemicals capable of redox chemistry, otherwise known as electrochemically responsive receptors, to detect different types of components in the patient, all of which are known in the art. It is also noted that the active electrode 104 can be substantially free of any substance or enzyme as taught by Jung, S. K. et al., *Analytical Chemistry*, 71: 3642–3649 (1999); Gorski et al., *J. Electroanalytical Chem.* 425 (1–2): 191–199 (1997); and Zen et al., *Analyst*, 125 (12): 2169–2172 (2000), the entire contents of each being incorporated herein by reference.

For example, the device 100 can be used to measure electrochemically active components such as electrolytes, oxygen, nitric oxide, lactate, insulin, neurotransmitters, drugs, and other analytes in the patient's body, as well as other characteristics such as the pH level in the patient's blood, the patient's temperature, resistance of the patient's skin, and so on. The reaction that occurs on the active electrode 104 can thus be a direct measure of electro-active species such as oxygen, nitric oxide, and so on, or the reaction can rely on enzymes to enable electrochemical detection such as glucose oxidase, glucose dehydrogenase, lactate dehydrogenase, as discussed above. It is understood that the term analyte includes electrochemically active species present in the patient as well as electrochemically active reaction products or by-products of species present in the patient with substances in layer 126. Also, the device 100 can be configured with many types of materials, such as metals, ceramics, or plastics, and the electronics shown in FIG. 4 can be integrated into the device 100, if desired. Additionally, device 100 can be integrated with any drug delivery device. Drug delivery devices include infusion, pump, transdermal, syringe, gas-assisted particle injectors, electroporation, intra- and interdermal injection devices for introducing liquid, particles, suspensions, emulsions, nanoparticles, micelles, liposomes and the like. Additionally, device 100 can be integrated with any drug delivery device to provide "closed-loop" control of monitoring and delivery of drugs, nucleic acids, or proteins.

Figure 7:
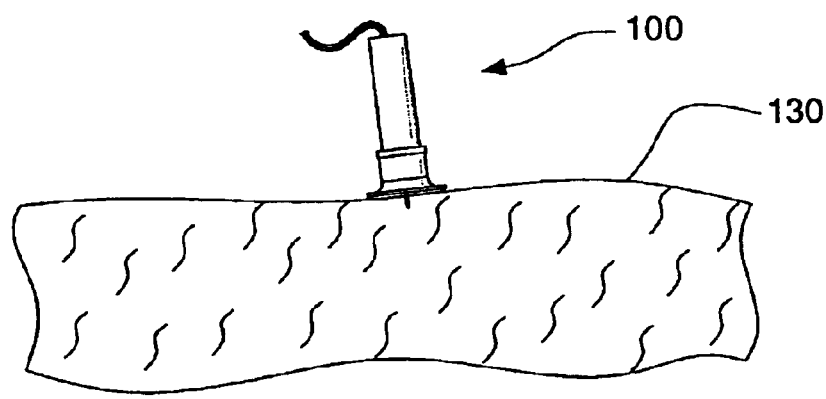
FIG. 7 illustrates an example of the manner in which the analyte detecting device shown in FIG. 1 is used on a patient.

The operation of the device 100 will now be described. As shown in FIG. 7, when the device 100 is used to detect the analyte of interest in the patient, the active electrode 104 and auxiliary electrode 106 can be brought into contact with the surface of a patient's skin 130, such as the surface of the patient's arm. By extending active electrode 104 from the base portion 102 either with mild pressure or by way of mechanical means, the active electrode 104 will pass through the stratum corneum of the patient's skin 130, while the auxiliary electrode 106 will rest on the surface of the patient's skin 130. It is noted that since the length of the active electrode 104 is small, for example 100–2000 μm, the active electrode 104 will only penetrate minimally into the patent's skin 130, and will reduce or eliminate substantially the tendency of the patient to bleed, nor will it contact the nerve endings in the patient's skin 130 to cause the patient discomfort. In an alternative embodiment, a plurality of active electrodes 104 are provided suitable for indexing sequentially within the base portion 102 and auxiliary electrode 106 for use followed by storage of used active electrodes for ease and save disposal thereof. Indexing of the plurality of electrodes is achieved using mechanical means suitable for such manipulation as known in the art.

Once through the stratum corneum, the active electrode 104 or the substance adjacent thereto electrochemically interacts with analyte in the tissue, or blood or interstitial fluid thus providing a detectable signal. For example, when the substance is glucose oxidase and the analyte is glucose, when the device 100 is placed against the skin and active electrode 100 is passed through the stratum corneum to a depth sufficient to access the analyte, the following electrochemical reaction occurs:

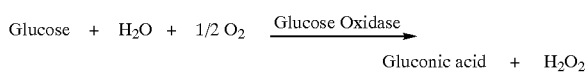

As can be appreciated by one skilled in the art, in accordance with the above reaction, oxygen is converted to hydrogen peroxide ($H_2O_2$) in the absence of mediators. The potentiostat 114 (see FIG. 4) can then be controlled to apply a potential to the active electrode 104 to place the active electrode 104 at an effective electric potential relative to the electrical potential of the patient's skin and preferably relative to the electrical potential of the auxiliary electrode 106. By effective electric potential, it is understood to mean a potential suitable to oxidize any or all of the electrochemically active analyte or species, for example, hydrogen peroxide generated by the glucose-glucose oxidase reaction set forth above, and induce a measurable electrical current to flow through the device 100 and, in particular, through the patient's skin 130 between the active electrode 104 and auxiliary electrode 106. The effective electric potential, as is known in the art, is dependent on the metal substrate 124 chosen. The applied effective potential may be applied in a variety of ways as required by the specific application, including but not limited to ramped, stepped, pulsed, programmed pulse, and combinations thereof.

Figure 8:
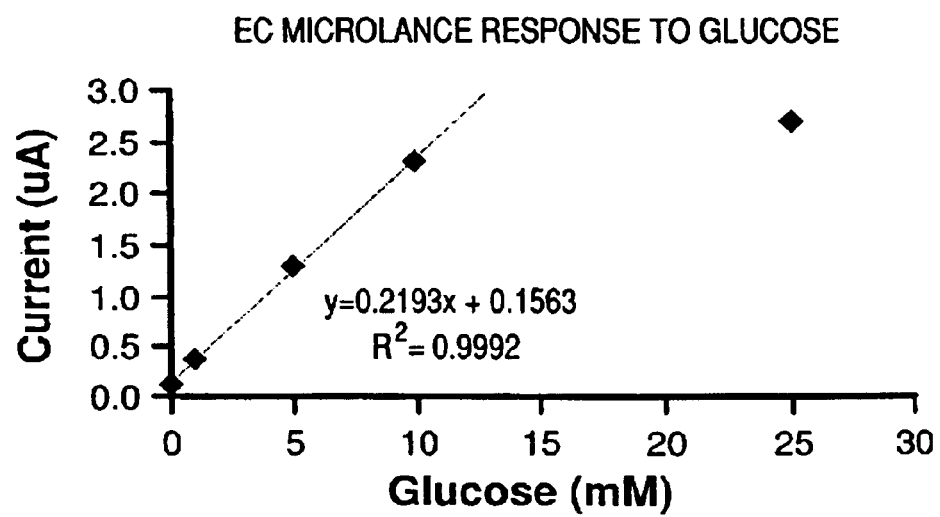
FIG. 8 is a graph showing an example of the relationship between current passing through the device shown in FIG. 1 and the glucose concentration in the environment in which the active electrode is inserted.

The magnitude of this current is related to the concentration of glucose in the patient. As shown, for example, in the graph of FIG. 8, the magnitude of current increases as the glucose level increases. Current detector 116 can monitor the current that is flowing thought the device 100. The current detector can be coupled to a controller (not shown), such as a microcomputer, which interprets the current in accordance with the graph shown in FIG. 8 to determine glucose level in the patient's blood. The detector can be configured as is known in the art to measure current or charge directly, or derivatives thereof.

It is further noted that variations in the condition of the patient's skin 130 can possibly affect the accuracy of the readings, because such variations can alter the level of current flow. As discussed in the example above, the active electrode 104 must be maintained at a specific electrical potential relative to the surrounding medium, for example, the patient's skin. This potential is typically within the range from at or about −0.6 V to at or about +0.6 V, depending on the electrochemistry of the analyte at the active electrode 104 and the nature of the metal substrate 124. Because the auxiliary electrode 106 is separated from the active electrode 104 by a certain distance (e.g., up to about 1 centimeter), a voltage drop (an "IR" drop) occurs between the active electrode 104 and the auxiliary electrode 106 due to the resistance of the patient's skin between these electrodes when the device 100 is applied to the patient's skin. Furthermore, because this IR drop varies due to a multitude of skin conditions and characteristics of the electrodes 104 and 106, the auxiliary electrode 106 may not be suitable as a reference potential for the electrical potential applied to the active electrode 104.

Accordingly, as shown by way of example in FIG. 9, the device 100 can include a reference electrode 132 positioned near to or adjacent the active electrode 104, so that the reference electrode 132 is in the electric field that is generated between the active electrode 104 and auxiliary electrode 106. This reference electrode 132 is electrically coupled to the power supply. However, the reference electrode can be integral with and electrically isolated from either the active electrode or the auxiliary electrode. For example, the tip portion of probe 120 of the active electrode 104 (See FIGS. 5 and 6) can have the reference electrode adjacent the active electrode on one side only or side by side on the same side, provided they are electrically isolated (from active electrode). Because the reference electrode 132 is positioned close to the active electrode 104 and thus, only a slight amount of the patient's skin is present between these electrodes when the device 100 is placed on the patient's skin 130, there is only a negligible IR drop between the active electrode 104 and the reference electrode 132 due to the patient's skin 130. Furthermore, since the IR drop is negligible, variations in skin conditions have little overall effect on the magnitude of this IR drop, thus ensuring that the correct electrical potential is being applied to the active electrode 104 during the measurement. For example, the probe portion 120 of the active electrode 104 (see FIGS. 5 and 6) can have the glucose oxidase coating on one side only, and an electrically isolated conductive coating on the other side to enable that side of the active electrode 104 to act as the reference electrode.

It is further noted that additional variations to the device 100 discussed above can be made. For example, the device 100 can have any suitable shape. As shown in FIG. 10, the device can have a cylindrical shape as does device 100-1, and can include multiple active electrodes 104-1, as well as one or more reference electrodes 132-1, surrounded by an auxiliary electrode 106-1. By employing multiple active electrodes 104-1, a plurality of parallel measurements can be taken, thus increasing the overall signal strength of the measurements without increasing pain to the patient. Alternatively, the multiple active electrodes 104-1 can be coated with different types or concentrations of enzymes as discussed above (or with none at all) to simultaneously detect different types of components or parameters as discussed above. In this arrangement, each different active electrode 104-1 is coupled, for example, to a respective input of a processor (not shown), or are otherwise discernable by the processor, so that the processor can interpret the different measurements.

In addition, the device 100 and its variations discussed above can be combined with a drug or medicament or medication delivery device, such as an insulin delivery device (not shown), which would automatically deliver the appropriate amount of insulin to the patient to correct the patient's blood glucose level. In other words, the device 100 and its variations can communicate with another instrument to recommend an action by the instrument or to adjust the action of an instrument. The device 100 and its variations can include a memory for storing information such as readings obtained by the device 100, or information provided by other instruments. Furthermore, the device 100 and its variations can be wearable like a watch or bracelet so that it can operation as a continuous or substantially continuous monitoring system.

The probe portion 120 active electrode 104 can also be coated with a sorbent coating so that when the active electrode 104 comes in contact with the fluid in the patient's skin 130, it immediately captures the fluid and therefore it does not have to reside in the patient's skin for a long period of time to take a reading. The active electrode 104 can be further configured as a hollow lumen, and the substance adjacent to the active electrode, such as for example glucose oxidase, can be placed inside the lumen. In this configuration, multiple openings can be placed in the lumen to allow free and rapid penetration of the component of interest (e.g., glucose) in the patient's skin 130 to enter the lumen. In this lumen configuration, selective layers can be placed over the openings or as a coating over the device 100 to prevent interfering species, such as ascorbate, urate, and acetaminophen, from encountering the active electrode 104.

Figure 12:
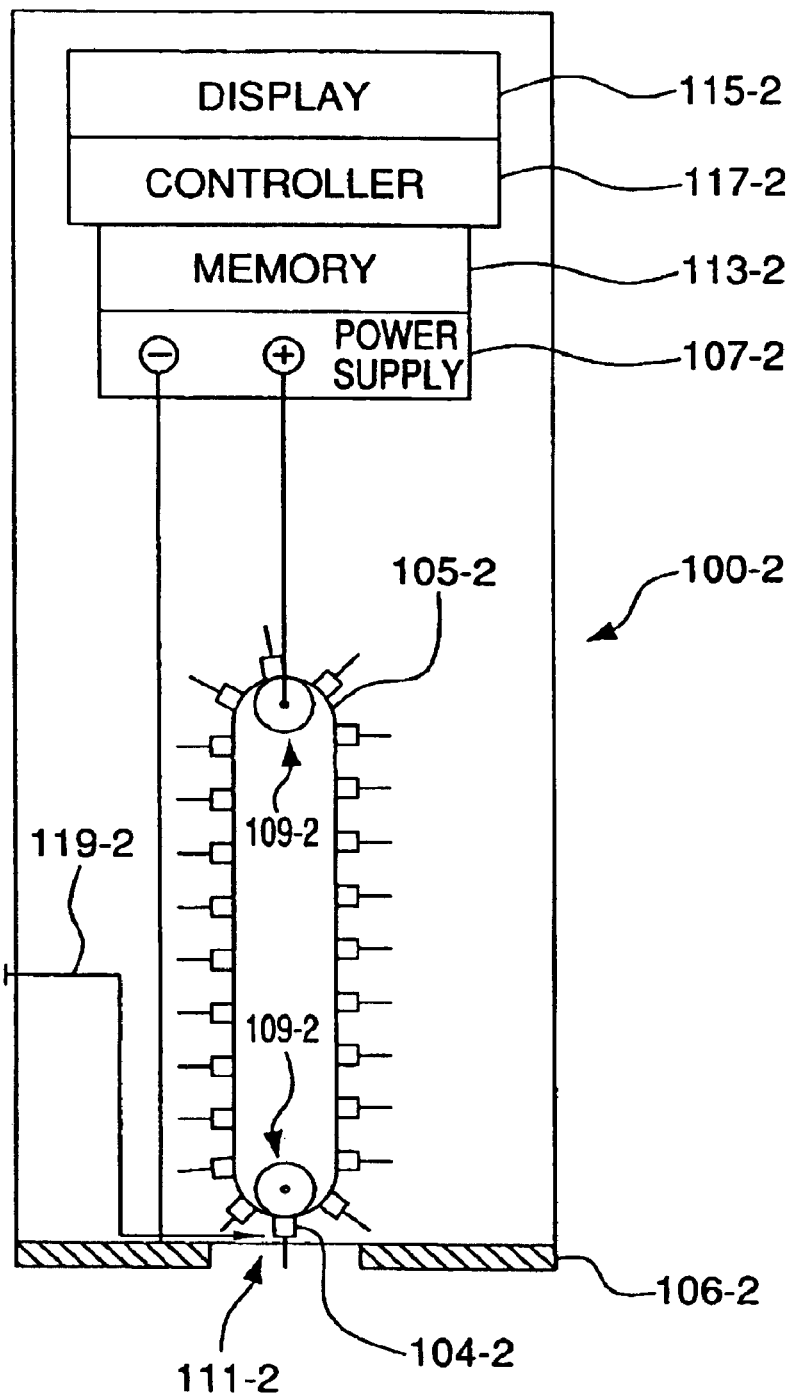
FIG. 12 illustrates a cross-sectional view of another example of a analyte detecting device as shown in FIG. 1 modified to include an active electrode dispenser according to another embodiment of the present invention

As shown in FIG. 11, multiple active electrodes 104-2 can be configured along a strip 105-2, which can be employed in an alternative configuration of the device 100-2 as shown in FIG. 12. That is, the device 100-3 can be configured as a dispenser for dispensing a plurality of active electrodes 104-2. As indicated, the strip 105-2 of active electrodes 104-2 can be loaded into the device 100-2 so that the device 100-2 thus contains a plurality of active electrodes 104-2 that can be fed sequentially as needed to provide a sterile, disposable component capable of storing the microprobes after use to minimize accidental injury. The device 100-2 further includes an auxiliary electrode 106-2 which can be similar to the auxiliary electrodes discussed above. The device 100-2 can further include a power supply 107-2 for providing an electrical potential across the active electrodes 104-2 and the auxiliary electrode 106-2.

That is, as indicated, the active electrodes 104-2 can be coupled to the strip 105-2 that is capable of conducting current from the anode of the power supply 107-2 to the active electrodes 104-2. A cartridge changing button (not shown) can be pressed to rotate the strip 105-2 about pulleys 109-2 to place another active electrode 104-2 at the active location 111-2 for taking a reading. The device 100-2 further includes a memory 113-2 for storing readings that have been taken in the manner described above for device 100, a display 115-2 for displaying the readings, and a controller 117-2 for controlling the operations of the power supply 107-2, memory 113-2, display 115-2 and any of the other components discussed above. The device 100-2 also includes an active electrode extender shown schematically as item 119-2 in FIG. 12, which can be controlled to extend and retract the active electrode 104-2 out from and into the device 100-2, respectively, for use. The extender 119-2 can further be configured to eject the active electrode 104-2 after use as can be appreciated by one skilled in the art. The auxiliary electrode 106-2 can be similarly extendable and retractable.

It is also noted that each active electrode 104-2 can be configured to have a portion which acts as the active electrode, and another portion, electrically isolated from the active electrode portion, that acts as a reference electrode like reference electrode 132 discussed above. In this arrangement, the strip 105-2 can be divided into two electrically isolated sections, one of which contacting the active portion of the active electrodes 104-2 and the other contacting the reference electrode portion of the active electrodes 104-2. The pulleys 109-2 can likewise be segregated to conduct separate paths of current to the separate portions of the strip 105-2 and thus, to the active and control portions of the active electrodes 104-2. The controller 115-2 can thus distinguish from the currents flowing through the active and control portions of the active electrode 104-2.

In addition, the device 100-2 can be configured to perform all the functions discussed above with regard to device 100 discussed above, to detect all of the components as discussed above. Also, the device 100-2 can be configured to communicate with another instrument to recommend an action by the instrument or to adjust the action of an instrument. Furthermore, the device 100-2 can be wearable like a watch or bracelet so that it can operation as a continuous or substantially continuous monitoring system.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. A device for detecting at least one analyte in a patient, comprising:

a plurality of active electrodes, said active electrodes having a length such that said active electrodes are adapted to pass through the stratum corneum to a depth which is sufficient to access said analyte and less than a depth in the dermis at which nerve endings reside, to enable the electrochemical detection of said analyte; and auxiliary electrodes configured to at least partially surround each of said active electrodes, and adapted to contact the surface of patient's skin when the device is placed against said patient and operated to detect said at least one analyte;

wherein said plurality of active electrodes are adapted to be sequentially positioned at at least one active location of said device.

2. A device as claimed in claim 1, wherein:

said auxiliary electrode has an abraded surface which is adapted to contact said patient's skin.

3. A device as claimed in claim 1, further comprising:

a data storage, adapted to store information pertaining to said at least one analye or said patient.

4. A device as claimed in claim 1, further comprising:

a communication device, adapted to communicate information between said device and an external device.

5. A device as claimed in claim 1, wherein:

said device is adapted for wearing by said patient for a duration of time.

6. A device as claimed in claim 1, wherein:

said analyte is electrochemically active.

7. A device as claimed in claim 1, wherein:

said analyte is selected from nitric oxide, neurotransmitters, insulin, and oxygen.

8. A device as claimed in claim 1, wherein:

said plurality of active electrodes are contained after use.

9. A device as claimed in claim 1, further comprising:

a delivery device integral therewith.

10. A device as claimed in claim 9, wherein:

said device and said delivery device are adapted to communicate with each other to control administration of a substance that said delivery device delivers to said patient.

11. A device for detecting at least one analyte in a patient, comprising:

a plurality of active electrodes having a length such that said active electrodes are adapted to pass through the stratum corneum of said patient to a depth which is sufficient to access said analyte and less than a depth in the dermis at which nerve endings reside; and at least one substance adjacent to at least a portion of said active electrodes capable of reacting with at least one analyte to produce at least one electrochemically active product; and auxiliary electrodes configured to at least partially surround each of said active electrodes, and adapted to contact the surface of said patient's skin when the device is placed against said patient and operated to detect said at least one analyte;

wherein said plurality of active electrodes are adapted to be sequentially positioned at at least one active location of said device.

12. A device as claimed in claim 11, wherein:
said auxiliary electrode has an abraded surface which is adapted to contact said patient's skin.

13. A device as claimed in claim 11, further comprising:
a data storage, adapted to store information pertaining to said at least one analye or said patient.

14. A device as claimed in claim 11, further comprising:
a communication device, adapted to communicate information between said device and an external device.

15. A device as claimed in claim 11, wherein:
said device is adapted for wearing by said patient for a duration of time.

16. A device as claimed in claim 11, wherein:
said substance is selected from glucose oxidases, glucose dehydrogenases, and electrochemically responsive receptors.

17. A device as claimed in claim 11, wherein:
said plurality of active electrodes are contained after use.

18. A device as claimed in claim 11, further comprising:
a delivery device integral therewith.

19. A device as claimed in claim 18, wherein:
said device and said delivery device are adapted to communicate with each other to control administration of a substance that said delivery device delivers to said patient.

20. A device for detecting at least one analyte in a patient, comprising:
a plurality of active electrodes adapted to be sequentially positioned at at least one active location of said device, each said active electrode having a length such that said active electrode is adapted to pass through the stratum corneum to a depth which is sufficient to access said analyte to enable the electrochemical detection of said analyte; and auxiliary electrodes configured to at least partially surround each of said active electrodes, and adapted to contact patient's skin when the device is placed against said patient.

21. A device as claimed in claim 20, wherein:
said plurality of active electrodes are contained after use.

22. A device for detecting at least one analyte in a patient, comprising:
a plurality of active electrodes adapted to be sequentially positioned at at least one active location of said device each said active electrode having a length such that said active electrode is adapted to pass through the stratum corneum of said patient to a depth sufficient to access said analyte; and at least one substance adjacent to at least a portion of said active electrode capable of reacting with at least one analyte to produce at least one electrochemically active product; and auxiliary electrodes configured to at least partially surround each of said active electrodes, and adapted to contact patient'skin when the device is placed against said patient.

23. A device as claimed in claim 22, wherein:
said plurality of active electrodes are contained after use.

* * * * *